| United States Patent [19] | [11] Patent Number: 4,886,787 |
|---|---|
| de Belder et al. | [45] Date of Patent: Dec. 12, 1989 |

[54] METHOD OF PREVENTING ADHESION BETWEEN BODY TISSUES, MEANS FOR PREVENTING SUCH ADHESION, AND PROCESS FOR PRODUCING SAID MEANS

[75] Inventors: Anthony N. de Belder; Thomas Mälson, both of Uppsala, Sweden

[73] Assignee: Pharmacia AB, Upsala, Sweden

[21] Appl. No.: 847,171

[22] PCT Filed: Jul. 16, 1985

[86] PCT No.: PCT/SE85/00282
§ 371 Date: Jan. 23, 1986
§ 102(e) Date: Jan. 23, 1986

[87] PCT Pub. No.: WO86/00912
PCT Pub. Date: Feb. 13, 1986

[30] Foreign Application Priority Data
Jul. 23, 1984 [SE] Sweden ................... 8403817

[51] Int. Cl.$^4$ .................. A61K 31/70; C07H 3/00
[52] U.S. Cl. ........................... 514/57; 514/54; 514/59; 514/60; 514/62; 536/55.1; 536/55.2; 536/56; 536/58; 536/106; 536/112
[58] Field of Search ............... 536/55.1, 55.2, 112, 536/56, 58, 106; 514/57, 54, 59, 60, 62

[56] References Cited

U.S. PATENT DOCUMENTS

| 3,275,576 | 9/1956 | Flodin et al. | 536/112 |
|---|---|---|---|
| 3,542,759 | 11/1970 | Gelotte et al. | 536/112 |
| 4,002,173 | 1/1977 | Manning et al. | 514/60 |
| 4,011,392 | 3/1977 | Rudolph et al. | 536/108 |
| 4,152,170 | 5/1979 | Nagase et al. | 536/1.1 |
| 4,174,440 | 11/1979 | Fujita et al. | 536/1.1 |
| 4,198,968 | 4/1980 | Kälberer et al. | 128/156 |
| 4,225,580 | 9/1980 | Rothman et al. | 514/60 |
| 4,605,691 | 8/1986 | Balazs et al. | 536/4.1 |

OTHER PUBLICATIONS

Laurent et al., *Acta Chemica Scandinavica* vol. 18, 1969, part 1, p. 279.

*Primary Examiner*—Ronald W. Griffin
*Assistant Examiner*—Elli Peselev
*Attorney, Agent, or Firm*—Fred Philpitt

[57] ABSTRACT

The invention is concerned with a method of preventing adhesions or accretions of body tissues inter se by means of employing a degradable gel of a crosslinked carboxyl-containing polysaccharide. The invention also covers a gel product to be used for this purpose, and a process for preparing said product by means of crosslinking with a di- or polyfunctional expoxide at a pH of from 2 to 5.

16 Claims, No Drawings

METHOD OF PREVENTING ADHESION BETWEEN BODY TISSUES, MEANS FOR PREVENTING SUCH ADHESION, AND PROCESS FOR PRODUCING SAID MEANS

This invention is concerned with a method of preventing adhesions or accretions of body tissues inter se with the aid of a degradable gel of a crosslinked polysaccharide containing carboxyl groups. The invention also comprises a gel product which is suited to this purpose, and a process for producing that gel product.

In many instances of practical surgery, it is highly desirable to have a simple means and method for preventing direct contact between tissues and for maintaining this contact-inhibiting effect also during a postoperative period the length of which will vary according to the actual type of surgery involved. Examples of such surgical procedures are manifold, spanning over a wide field: E.g. operations performed in abdominal regions where it is important to prevent adhesions of the intestine or the mesentery with concomitant gastrointestinal disorders; operations performed in the urogenital apparatus where it is important to ward off adverse effects on the ureter and bladder, and on the functioning of the oviduct and uterus; and nerve surgery operations where it is important to minimize the development of granulation tissue. When tendons are operated on there is generally a tendency towards adhesion between the tendon and the surrounding sheath or other surrounding tissue during the immobilization period following the operation. Essentially unsuccessful attempts have been made to solve this problem by using various kinds of sutures and by means of passive movements of the tendon during the healing process. In ophthalmological surgery it is often desirable to have degradable implants at one's disposal which are to be applied in the angle of the anterior chamber of the eye for the purpose of preventing synechiae between the cornea and the iris; this applies especially in cases of reconstructions after severe damaging events. Moreover degradable or permanent implants are often desirable means for preventing adhesion in e.g. glaucoma surgery contexts (preventing adhesion in the subconjunctival filtration space) and in strabismus surgery.

Tubular implants may be employed for obtaining an improved flow from the anterior chamber, for thwarting obstruction of the lachrymal duct, and for improving the result of dacryocystorhinostomy.

In one particular type of articular surgery described by Engkvist et al. in Scand. J. Plast. Reconstr Surg. 14 (1980), 71-87, silicone plates Silastic ½ (Dow Corning) are introduced surgically in order to prevent accretions of cartilaginous tissue. After some 12 to 16 weeks, however, it is necessary to again remove the implant surgically. Thus, the techniques presently available necessitate removal of the inserted material after a suitable period of time in all cases where this material has to be of a rigid type for the sake of securing a high degree of mechanical stability. In other cases, where mechanical stability is not a major factor, it has been customary to use non-crosslinked dextran or hyaluronic acid. But even if a substance of such high viscosity as hyaluronic acid is used for application to contact surfaces the protection period thus obtained is too short to be satisfactory.

What is needed is therefore a product which is applicable in a suitable form for preventing adhesions and accretions between tissues and which optionally is to have the property of being degradable after a desired period of time.

We have now found that a gel of a crosslinked carboxyl-containing polysaccharide is exceedingly suitable for being used as a degradable implant.

The present invention is thus concerned with a novel degradable gel consisting of a polysaccharide which contains carboxyl groups—such as for example carboxymethyl starch, carboxymethyl dextran, carboxymethyl cellulose and glucosaminoglycans such as e.g. heparin, heparan sulfate, chondroitin sulfate and hyaluronic acid—and which has been crosslinked with a di- or polyfunctional epoxide. Examples of such epoxides are 1,4-butanediol diglycidyl ether (BDDE), 1,2-ethanediol diglycidyl ether (EDDE), 1-(2,3-epoxypropyl)-2,3-epoxycyclohexane (Bakelite epoxy resin ERL 4206, Union Carbide), N,N-diglycidyl aniline (Leuktherm X 50, Bayer), and epoxy-substituted pentaerythritol (Shell 162). These crosslinking reagents and other suitable epoxy compounds are well known to persons skilled in the art. The same applies to the choice of polysaccharides available which either contain carboxyl groups from the outset or may be derivatized so as to then contain such groups. The crosslinking has been carried out in an acidic medium, in the presence of an acidic catalyst. A great number of substances have been found to act as catalysts in the crosslinking reaction. Examples of such substances are inorganic acids such as e.g. sulfuric acid, nitric acid, hydrochloric acid and phosphoric acid; furthermore organic mono- and polycarboxylic acids, e.g. lower aliphatic acids such as for instance formic acid, acetic acid, propionic acid, lactic acid, trichloroacetic acid, succinic acid, and aromatic mono- or polyfunctional carboxylic acids or sulfonic acids, e.g. benzoic, salicylic and paratoluenesulfonic acids. The term "polycarboxylic acids" comprises all acids having more than one carboxyl group. It is possible to replace the free acids employed by their hydrogen salts in those cases where such salts can be formed.

The present invention also relates to a process for producing a degradable gel by means of reacting a carboxyl-containing polysaccharide with a bi- or polyfunctional epoxide at a pH of from 2 to 5, preferably from 2.5 to 4.5, in the presence of an acidic catalyst of the aforesaid type.

In a preferred embodiment of the invention the carboxyl-containing polysaccharide is hyaluronic acid or a salt thereof such as the sodium salt. Hyaluronic acid exists in a wide range of forms of different molecular weights depending on its source and on the purification methods employed. Products within the range of 20,000 to 5,000,000, in particular 500,000 to 3,000,000, are suitable for producing gels according to this invention. In cases where the molecular weight exceeds $10^6$ the concentrations of such hyaluronic acids in the reaction mixture may suitably be 5 to 10% by weight. Considerably higher concentrations have to be employed for achieving gel formation with low molecular polysaccharide starting materials. Similarly, the amount of crosslinking agent may be varied within a very broad range, from about 10 to about 500% by weight of the hyaluronic acid, depending on the particular properties desired in the gel. The reaction may advantageously be performed at an elevated temperature of 30° to 80° C., although temperatures of 30°-50° C. are preferred for minimizing the risk of acid hydrolysis. As regards the reaction time, this is usually chosen within the range of from 3 to 20 hours, a preferred range being 5 to 15 hours.

The dry solids content of a gel swelled in physiological saline will preferably be within the range of from 0.5 to 10% by weight.

IR analysis of a gel produced in a manner analogous to that of Example 1 below showed a significant peak in its IR spectrum at about 1745 cm$^{-1}$, which is characteristic of an O-ester group. This peak remained in the spectrum also after the gel had been treated with phosphate buffer (pH 6.8); in that stage most of the carboxyl groups are ionized and thus unable to contribute to the aforesaid peak. These results indicate, thus, that the acid-catalyzed gels do contain O-ester bridges. Gels produced by means of alkaline catalysis (see for instance Laurent et al., Acta Chim. Scand. 18 (1964) 274-275) do not show such a peak at 1745 cm$^{-1}$.

The novel gels of this invention are degradable; a hyaluronate gel implanted in a rat was found to undergo slow swelling while at the same time gradually loosing its shape and rigidity. After 32 hours the gel had lost its integrity (intactness). Such gels therefore are suitable to be used in cases where the contact-inhibiting effect is to be upheld for several days.

If it is desired that the contact-inhibiting effect is maintained during a considerably longer period of time the gel to be chosen will e.g. be one according to the present invention having a high degree of crosslinking or will be an alkali-catalyzed gel of the type described in the Swedish patent application No. 8403090-7. Crosslinked hyaluronic acid gels of these types, especially those according to said Swedish patent application, will degrade quite slowly; their contact-inhibiting effect may therefore persist for several months. In so far as said Swedish patent application describes the use of certain alkali-catalyzed gels as vitreous humor substitutes, this is not comprised by the present invention.

The gels may be prepared in many different forms depending on the particular use to which they are to be put. When the individual components have been added, the reaction mixture is transferred to a suitable container in which the polymerized product will be given its desired form, e.g. thin layers, rods, tubes. After the polymerization step, the gel may be crushed if desired; this will result in a product suitable to be injected into the space or cavity to be filled out by the gel.

It is imperative to have the polysaccharide duly purified from components that might otherwise cause toxic or undesired immunological reactions. Similarly, it is necessary that the final gel be liberated by careful washing from e.g. unreacted crosslinking reagent. The gel may be sterilized and autoclaved. To carry out the method of this invention for preventing mutual adhesion or accretion (synechia) of body tissues, one or more pieces of the gel are introduced, during the course of the surgical operation, into the interstice between the tissues to be maintained in a separated condition The gel that is thus introduced may be partially swollen in a physiologically acceptable solution. Alternatively, the swollen gel may be injected in a crushed form into the site where the adhesion-inhibiting effect is desired.

EXAMPLES

1. Preparation of gels of crosslinked hyaluronic acid 1 (a) 400 mg of sodium hyaluronate having a molecular weight of about $3 \times 10^6$ was dissolved in 4 ml of distilled water in a plastic test tube. After about 2 hours, 600 µl of 1,4-butanediol diglycidyl ether (BDDE) was added and then, after agitation, 150 µl of glacial acetic acid. The mixture was left standing for 15 hours at 60° to 70° C., whereupon the gel thus formed was washed with water. The solids content of the swollen gel was 3.3% (% by weight of swollen gel in physiological saline).

1 (b) The process of Example 1 (a) was repeated but with 200 µl of BDDE and 200 µl of glacial acetic acid, and with a reaction time and temperature of 5 hours and 50° C. respectively. The gel had a solids content of 5.0%.

1 (c) The process of Example 1 (a) was repeated but with 600 mg of sodium hyaluronate, 400 µl of BDDE and 200 µl of glacial acetic acid. The gel had a solids content of 8.4%.

1 (d) The process of Example 1 (a) was repeated but with 400 mg of sodium hyaluronate having a molecular weight of about $1 \times 10^6$ and with 150 mg of lactic acid as the catalyst. The resultant gel had a solids content of 1.6%.

1 (e) The procedure of Example 1 (a) was also repeated with the following catalysts: 400 µl of 2N sulfuric acid, 200 µl of 50% trichloroacetic acid and, respectively, 200 µl of a solution of 1.5 g of benzoic acid in 1.5 ml water and 1.5 ml dimethyl sulfoxide.

In all of these cases a gel of crosslinked hyaluronate was obtained.

1 (f) 150 mg of sodium hyaluronate having a molecular weight of about $3 \times 10^6$ was dissolved in 1.5 ml of water. When the solution was homogeneous 75 µl of glacial acetic acid and 75 mg of epoxy-substituted pentaerythritol (Shell 162, degree of substitution about 3.5) were added. The mixture was left standing overnight at 60° C., whereupon the gel thus formed was washed with water. The swollen gel had a solids content of 2.4%.

1 (g) The procedure according to Example 1 (a) was repeated, but with 75 mg of N,N-diglycidyl aniline (Leuktherm X50, Bayer) as the crosslinking reagent and with 400 µl of 2N sulfuric acid as the catalyst. The gel had a solids content of 3.7%.

1 (h) The procedure of Example 1 (a) was repeated, but with 200 mg of sodium hyaluronate of moleular weight about 500,000, 250 µl BDDE and 100 µl glacial acetic acid. The reaction was allowed to proceed overnight at 50° C. This experiment resulted in the formation of a crosslinked hyaluronic acid gel, and the same applies to another run where 200 mg of hyaluronic acid (free acid form) having a molecular weight of about $3 \times 10^6$ was reacted with 200 µl of BDDE in the presence of 100 µl glacial acetic acid.

1 (i) Experiments were run in a manner analogous to that of Example 1 (a) but employing in one case 300 mg of sodium hyaluronate and 150 µl of BDDE in the presence of 150 µl of glacial acetic acid and in the other case 300 mg of sodium hyaluronate and 250 µl of BDDE in the presence of 250 µl of glacial acetic acid. Gels were obtained in which the content of crosslinking agent amounted to 9 and 21% by weight respectively as measured by GLC.

2 Preparation of gels of crosslinked carboxymethyl dextran, carboxymethyl cellulose, and chondroitin sulfate 2 1 (a) 600 mg of carboxymethyl dextran having a molecular weight of about $2 \times 10^6$ was dissolved in 3 ml of water. Next 300 µl of BDDE and 300 µl of glacial acetic acid were added, whereupon the mixture was left standing overnight at 50° C. The gel that had formed by then was washed with water.

2 (b) 400 mg of carboxymethyl cellulose (Fluka CMC sodium salt) was dissolved in 3 ml of water, whereafter the reaction was carried out as in Example 2 (a) but with 200 μl of BDDE and 200 μl of glacial acetic acid. An opalescent elastic gel was obtained.

2 (c) 800 mg of chondroitin sulfate (sodium salt, Sigma) was dissolved in 2 ml of water, whereafter the reaction was carried out as in Example 2 (a) but with 200 μl of BDDE and 100 μl of glacial acetic acid. A gel of firm consistency was obtained.

3. Preparation of an alkali-catalyzed gel of crosslinked hyaluronic acid 2.5 g of sodium hyaluronate having a molecular weight of $3 \times 10^6$ was dissolved in 18.75 ml of 0.5% NaOH, with stirring, until a clear homogeneous solution was obtained. 0.94 ml of BDDE was added, and after thorough mixing the solution was introduced into a container in which a gel of desired shape was formed during 2 hours at 50° C. Before being used the gel was washed carefully and sterilized in an autoclave.

This is an example of the more stable type of gels of crosslinked carboxy-containing polysaccharide the preparation of which is described in detail in SE 8403090-7.

4. Degradation of a hyaluronate gel in vivo (rat)

A gel produced in the same manner as in Example 1 was shredded into small pieces. These were weighed and inserted into small Plexiglas ® chambers which were then covered with nylon net and implanted subcutaneously in rats. After suitable periods of time the gel pieces were removed, weighed and analyzed with respect to their hyaluronate contents, with the results[a] as set forth below. The hyaluronate content was determined in accordance with three mutually independent methods: The orcinol method (Mejbaum W., Physiol. Chem. 258 (1939), 117), the hyaluronidase method (Dische Z., J. Biol. Chem. 167 (1947), 189), and the carbazole method (Jourdian G.W. et al., Anal. Biochem. 96 (1979), 474). The results obtained with these three methods were in good agreement inter se, and for this reason only those obtained with the carbazole method are set forth below.

| Time, hours | Weight before implantation, mg | Weight after implantation, mg | Amount of hyaluronate remaining in gel, % of original |
|---|---|---|---|
| 0 | 133 | — | 100 |
| 0 | 131 | — | 100 |
| 24 | 144 | 206[b] | |
| 24 | 141 | 215[b] | 106 |
| 32 | 133 | 245[b] | |
| 32 | 128 | 259[b] | 89 |

[a] double samples were analyzed
[b] the samples had taken up water, resulting in a softer jelly consistency 5. Prevention of peritoneal ahesions with hyaluronate gel film Forty-eight Wistar male rats (250–300 g each) were used. Of these were three animals excluded because they did not survive the operation (one animal in the test group) or died from peritonitis during the first post-operative day (two animals in the control group).

Anaesthesia was accomplished with a 10% solution of etorfine and acepromazine (Immobilon ®, Pharmacia A/S) i.m. and postoperative reversal was achieved with a 10% solution of diprenorfine (Reuivon ®, Pharmacia A/S). Coeliotomy was performed through a 4-cm median incision. One cm to the right of the midline $1 \times 3$ cm of peritoneum and underlying muscle was excised. The peritoneal defect was then closed with seven atraumatic 3/0 single silk sutures. At this point of the procedure the animals were randomly allocated to a test group or a control group.

In the test group a hyaluronate gel film prepared according to examples 1a or 3 with the dimensions $2 \times 2$ cm was introduced between the exposed tissue surfaces.

On the seventh day all rats were sacrificed by ether exposure and the abdomen was opened through a left-sided curved incision. The sutured 3 cm long periforeal defect to the right of the midline was visualized and the part of the defect occupied by adhesions was measured in mm. The abdomen was then examined for pathological conditions other than adhesions.

In the test group, that is the hyaluronate gel film treated group, no adhesions were found.

In the control group adhesions involving the greater omentum, and in eight animals the small intestine as well, were present in all animals. The median length of attachment being 27 mm.

No pathological conditions other than adhesions, i.e. bowel obstruction, peritonitis, abscesses or fluid in the abdomen, were found.

6. Prevention of post-operative adhesions between tendon and tendon sheath

Six rabbits were used divided into a test group and a control group with three animals in each. In each animal two tendons in the fore paw were divided and the hyaluronate gel film, prepared according to examples 1b or 3, was folded around the tendon after that it had been rejoined with sutures. The tendon sheath was partly sealed. After four weeks, the animals were sacrificed and the operated tendons were inspected.

In the control group, most of the operated tendons presented adhesions to the surrounding tendon sheath. In the test group, however, the adhesions were very rare and of small size.

We claim:

1. A gel of sodium hyaluronate or hylaluronic acid cross-linked with a di- or polyfunctional expoxide at a pH within the range of from 2 to 5.

2. A process for preparing a gel consisting of a cross-linked carboxyl-containing polysaccharide selected from the group consisting of carboxymethyl dextran, carboxymethyl starch, carboxymethyl cellulose and glucosminoglycans formed by reacting the polysaccharide at a pH of from 2 to 5 with a bi- or polyfunctional epoxide in the presence of an acid.

3. A process according to claim 2 wherein said pH is in the range of 2.5 to 4.5.

4. The process according to claim 2 in which said acid is selected from the group consisting of inorganic acids, organic acids and hydrogen salts thereof.

5. A process according to claim 2 in which said acid is selected from the group consisting of hydrochloric, sulfuric, nitric or phosphoric acid, or a hydrogen salt thereof.

6. A process according to claim 2 in which said acid is selected from among (a) lower aliphatic mono- or polycarboxylic acids or (b) aromatic mono- or polycarboxylic acids and sulfonic acids, or (c) hydrogen salts of acids belonging to group (a) or (b).

7. A process according to claim 2 in which said acid is selected from the group consisting of formic, acetic, propionic, lactic, trichloroacetic, succinic, benzoic, salicylic and p-toluene sulfonic.

8. A process according to claim 2 wherein said polysaccharide is hyaluronic acid.

9. A process according to claim 2 wherein said polysaccharide is sodium hyaluronate.

10. A process according to claim 4 wherein said polysaccharide is sodium hyaluronate.

11. A process according to claim 5 wherein said polysaccharide is sodium hyaluronate.

12. A method of preventing adhesions or accretions of body tissues in which one or more pieces of a gel of a crosslinked carboxylgroup-containing polysaccharide selected from the group consisting of carboxymethyl dextran, carboxymethyl starch, carboxymethyl cellulose and glucosaminoglycans, during the course of a surgical operation, is introduced into the interstices between the tissues to be maintained in a separated condition; the gel being formed by reacting said polysaccharide with a bi- or polyfunctional epoxide.

13. A method according to claim 12 wherein the gel is formed by reacting the polysaccharide with a bi- or polyfunctional epoxide at a pH within the range of from 2 to 5.

14. A method according to claim 13 wherein said pH is from 2.5 to 4.5.

15. A method according to claim 12 wherein said polysaccharide is sodium hyaluronate.

16. A method according to claim 13 wherein said polysaccharide is sodium hyaluronate.

* * * * *